United States Patent [19]

Meguro et al.

[11] 4,235,775
[45] Nov. 25, 1980

[54] TRIAZOLOBENZODIAZEPINE DERIVATIVES

[75] Inventors: Kanji Meguro, Takarazuka; Yutaka Kuwada, Ashiya, both of Japan

[73] Assignee: Takeda Chemical Industries, Ltd., Osaka, Japan

[21] Appl. No.: 49,055

[22] Filed: Jun. 15, 1979

Related U.S. Application Data

[63] Continuation of Ser. No. 201,960, Nov. 24, 1971, abandoned.

[30] Foreign Application Priority Data

Dec. 11, 1970 [JP] Japan .................................. 45/110716

[51] Int. Cl.$^2$ ..................... A61K 31/55; C07D 487/04

[52] U.S. Cl. .......................... 260/243.3; 260/239 BD; 260/244.4; 260/245.5; 424/248.56; 424/267; 424/269

[58] Field of Search ............... 260/245.5, 243.3, 244.4, 260/245.7

[56] References Cited

U.S. PATENT DOCUMENTS 3,681,343  8/1972  Hester .............................. 260/245.5

FOREIGN PATENT DOCUMENTS 6916543  5/1970  Netherlands .......................... 260/245.5

*Primary Examiner*—Alton D. Rollins
*Attorney, Agent, or Firm*—Wenderoth, Lind & Ponack

[57] ABSTRACT

The invention relates to 1-aminomethyl-6-phenyl-4H-s-triazolo[4,3-a][1,4]benzodiazepine compounds useful as sedatives, tranquilizers, anticonvulsants or hypnotics, and processes for their production.

15 Claims, No Drawings

TRIAZOLOBENZODIAZEPINE DERIVATIVES

This is a continuation of application Ser. No. 201,960, filed Nov. 24, 1971, now abandoned.

The present invention relates to novel and useful triazolobenzodiazepine derivatives of the general formula (I)

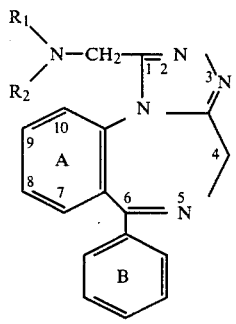

wherein $R_1$ and $R_2$ represent hydrogen or an alkyl group which is unsubstituted or substituted, and may form with the adjacent nitrogen atom a cyclic amino group which is unsubstituted or substituted, the rings A and B are unsubstituted or substituted by one or more halogen, nitro, trifluoromethyl, alkyl or alkoxy groups, and the nitrogen atom at the 5-position may be in the form of N-oxide, and pharmaceutically acceptable salts thereof.

The present invention also relates to intermediates for these derivatives and further relates to a method for the production of triazolobenzodiazepine derivatives of the general formula (I) and their intermediates.

There have been synthesized many kinds of 1,4-benzodiazepine derivatives, and some of them have been put into practical use as sedatives, and tranquilizers. However, most of these known 1,4-benzodiazepine derivatives are necessarily accompanied with muscle relaxing activity together with the desired tranquilizing and sedative activities, and by this muscle relaxing activity some undesirable side effect is caused. Therefore, it has long been a desideratum to remove or reduce the muscle relaxing activity in tranquilizers or sedatives.

Under these circumstances, the present inventors have made extensive studies for providing effective benzodiazepine derivatives accompanied with no such drawback as above.

As the result of the studies, the present inventors have succeeded in synthesizing novel triazolobenzodiazepine derivatives of the general formula (I) and found that these compounds can answer the purpose.

Namely, by introducing the aminomethyl group represented by the formula

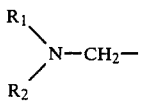

($R_1$ and $R_2$ have the same meaning as above) into the 1-position of the triazolo[4,3-a][1,4]-benzodiazepine structure, the muscle relaxing activity is rather reduced without sacrificing the desired activities such as sedative, psychosedative, anticonvulsive, tranquilizing and hypnotic activities.

The present invention has been accomplished on the basis of these findings.

Thus, the principal object of the present invention is to provide novel triazolobenzodiazepine derivatives useful as effective and improved sedatives, tranquilizers, anticonvulsants of hypnotics, and another object is to provide intermediates for these compounds. Further object is to provide a method for the production of these compounds and intermediates thereof.

Referring to the general formula (I), the alkyl groups represented by the symbols $R_1$ and $R_2$ may be any of straight, branched or cyclic ones having up to six carbon atoms and may be substituted by a hydroxy group in their optional position. The typical examples of the groups are methyl, ethyl, propyl, isopropyl, butyl, isobutyl, t-butyl, pentyl, hexyl, cyclopentyl, cyclohexyl, hydroxyethyl, hydroxypropyl, hydroxyisopropyl, hydroxycyclohexyl, etc. As the cyclic amino groups formed by $R_1$ and $R_2$ together with the adjacent nitrogen atom, there are mentioned 3- to 6-membered ones, desirably 5- to 6-membered ones, which may be substituted by an alkyl or hydroxyalkyl group in an optional position of the group. The alkyl or hydroxyalkyl groups as the substituents have the same meaning as those represented by the symbols $R_1$ and $R_2$, among which lower ones having 1 to 3 carbon atoms are preferable. The typical examples of the cyclic amino groups are ethyleneimino, pyrrolidino, piperidino, morpholino, piperazine, N-substituted piperazino[e.g. N-(2-hydroxyethyl)piperazino, N-(3-hydroxypropyl)piperazino, N-methylpiperazino, N-ethylpiperazino], etc. The rings A and B may be substituted by one or more halogen, nitro, trifluoromethyl, alkyl or alkoxy groups, which may be same or different, at optional position(s). The halogen atom includes chlorine, bromine, iodine and fluorine; the alkyl groups are preferably lower ones having up to three carbon atoms, such as methyl, ethyl, propyl, isopropyl; and the alkoxy groups are preferably lower ones having up to three carbon atoms, such as methoxy, ethoxy, propoxy, isopropoxy.

The compound of the general formula (I) can be produced by reacting at first a compound of the general formula (II)

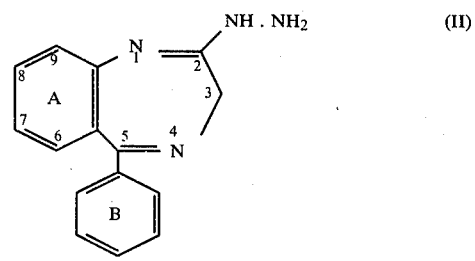

(wherein the rings A and B have the same meaning as above, and the nitrogen atom at the 4-position may be in the form of N-oxide) with a compound of the general formula (III)

$$X-CH_2-C(OR_3)_3 \qquad (III)$$

(wherein X is halogen, and $R_3$ represents a lower alkyl group) to give a compound of the general formula (IV)

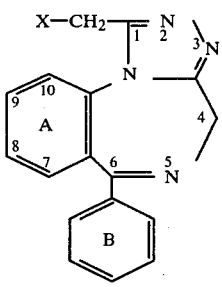

(IV)

(wherein X and the rings A and B have the same meaning as above, and the nitrogen atom at the 5-position may be in the form of N-oxide) [Step A], and then reacting the product (IV) with ammonia or a primary or secondary amine corresponding to the amino group represented by the formula

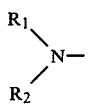

(wherein $R_1$ and $R_2$ have the same meaning as above) [Step B].

Referring to the general formulas (II), (III) and (IV), the halogen atom represented by the symbol X includes chlorine, bromine and iodine, and the lower alkyl group represented by the symbol $R_3$ has the same meaning as that in the substituent of the rings A and B.

[Step A]

The reaction of the Step A is carried out at room temperature or under ice-cooling preferably in the presence of a suitable solvent and a suitable acid catalyst. The solvent may, for example, be alcohols (e.g. methanol, ethanol), organic amines (e.g. pyridine), halogenated hydrocarbons (e.g. chloroform, dichloromethane), acid amides (e.g., dimethylformamide), etc., and the acid catalyst may, for example, be inorganic acids (e.g. hydrochloric acid, hydrobromic acid, sulfuric acid, etc.) and organic acids (e.g. acetic acid, monochloroacetic acid, p-toluenesulfonic acid, etc.). An amount of the compound (III) to be used is generally about 1 to about 10 moles per mole of the compound (II), and an amount of the acid catalyst is generally about 1 to about 5 moles per mole of the compound (II). In the reaction of this Step, it can be presumed that the compound (IV) is produced through an intermediate compound of the general formula (V)

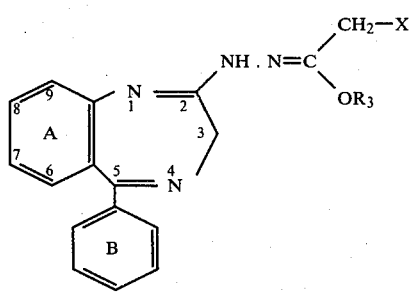

(V)

(wherein X, $R_3$ and the rings A and B have the same meaning as above, and the nitrogen atom at the 4-position may be in the form of N-oxide).

Thus produced compounds (IV) can be recovered as a free base or a suitable acid salt thereof in an optional purity by per se conventional methods [e.g. neutralization with a suitable basic substance (e.g. sodium carbonate, sodium bicarbonate) and extraction with a suitable solvent (e.g. chloroform, dichloromethane, ethyl acetate)].

[Step B]

The reaction of the Step B is carried out preferably in the presence of a suitable solvent at room temperature or under heating up to a boiling point of the solvent used, although the reaction can proceed even under cooling. The solvent may, for example, be hydrocarbons (e.g. benzene, toluene), esters (e.g. ethyl acetate) and those mentioned above as the reaction solvent of the Step A. An amount of the primary or secondary amine to be used, which corresponds to the amino group of the formula

(wherein $R_1$ and $R_2$ have the same meaning as above), is generally about 1 to about 10 moles per mole of the compound (IV). When ammonia is put into the reaction, however, it is preferable to use the same in a large excess amount.

Further, for the purpose of saving the amine to be used, it is preferable to add a suitable acid acceptor to the reaction system so as to eliminate a hydrogen halide produced. The acid acceptor may, for example, be organic amines (e.g. pyridine, triethylamine), alkalimetal carbonates or bicarbonates (e.g. sodium carbonate, potassium carbonate, sodium bicarbonate, potassium bicarbonate, etc.). In case where the compound (IV) is employed in a form of an acid salt, the acid salt may previously be converted to a free form by using the acid acceptor, and also in such a manner, an amount of the amine to be used can be saved.

In a case of employing the compound (IV) wherein X is chlorine or bromine, the reaction of the present Step can, occasionally, be carried out more advantageously by using a process comprising treating at first the compound wherein X is chlorine or bromine with an alkali metal iodide (e.g. sodium iodide, potassium iodide) or allowing the iodide to exist in the reaction system, whereby the compound (IV) wherein X is chlorine or bromine is converted to the compound (IV) wherein X is iodide and then subjecting thus converted compound (IV) to the reaction of the present Step.

The reaction of the Step A and the Step B can be conducted continuously by adding directly ammonia or the primary or secondary amine, if necessary, together with the acid acceptor mentioned above, to the reaction mixture of the Step A without isolation of the intermediate compound (IV) after completion of the reaction of the Step A.

Thus produced subject compounds (I) can be recovered in an optional purity by per se conventional methods (e.g. distillation, extraction with such a solvent as those mentioned in the extraction of the compounds (IV), recrystallization).

In case where the compounds (I) are obtained in a form of a free base, the compounds (I) can be converted to the acid salts thereof by per se conventional method using a suitable acid. The acid may, for example, be inorganic acids (e.g. hydrochloric acid, hydrobromic acid, sulfuric acid), organic acid (e.g. p-toluenesulfonic acid, oxalic acid, malonic acid, succinic acid, tartaric acid, malic acid).

In case where the nitrogen atom at the 5-position of the compounds (I) is in the form of N-oxide, the oxygen atom may be removed, if necessary, by reduction with a suitable deoxygenating agent such as phosphorus trihalide (e.g. phosphorus trichloride), or by catalytic hydrogenation using Raney nickel or chemical equivalents thereto.

Thus produced compounds (I) and acid salts thereof are novel compounds and show low muscle relaxing activity and relatively high sedative, tranquilizing, psychosedative, anticonvulsive and hypnotic activities. Therefore, these compounds are useful as medicines such as sedatives, tranquilizers, anticonvulsants, hypnotics with only a slight side effect caused by muscle relaxing action.

These compounds can be used orally or parenterally per se or, if desired, in a suitable pharmaceutical form such as powder, granules, tablets, injections admixed with a pharmaceutically acceptable inert carrier.

Especially, the acid salts of the compounds (I) are generally soluble in water and can be used advantageously in a form of injections or syrups.

The dose of these compounds to be administered varies with the kinds of the compounds, the conditions of the diseases, etc., and generally falls within the range of from about 1 mg. to about 30 mg. for oral administration, and from about 1 mg. to about 20 mg. for parenteral administration for an adult human per day.

For further explanation of the present invention, the following Examples are given, wherein the word "part(s)" is based on weight unless otherwise noted and relationship between "part(s)" and "volume part(s)" corresponds to that between "gram(s)" and "milliliter(s)."

EXAMPLE 1

To a mixture of 1.5 parts of 7-chloro-2-hydrazino-5-phenyl-3H-1,4-benzodiazepine 4-oxide, 3.6 parts of ethyl orthobromoacetate and 25 volume parts of ethyl alcohol is added dropwise 0.5 volume part of sulfuric acid under stirring, followed by stirring for further 30 minutes. The separated crystals are collected by filtration and recrystallized from dimethylformamide-water to give 1-bromomethyl-8-chloro-6-phenyl-4H-s-triazolo[4,3-a][1,4]benzodiazepine 5-oxide as colorless flakes melting at 249° to 251° C. (decomposition).

EXAMPLE 2

The same compound as obtained in Example 1 is also prepared by using methyl orthobromoacetate instead of ethyl orthobromoacetate. Melting point 249° to 251° C. (decomposition).

EXAMPLE 3

To a solution of 3.34 parts of 2-hydrazino-5-phenyl-7-trifluoromethyl-3H-1,4-benzodiazepine 4-oxide and 8.0 parts of methyl orthobromoacetate in 40 volume parts of chloroform is added portionwise 3.8 parts of p-toluenesulfonic acid hydrate with stirring under ice-cooling. The mixture is further stirred for one hour at room temperature and then 30 volume parts of a saturated aqueous sodium bicarbonate solution is added to the reaction mixture. After a few minutes' stirring, precipitated product is filtered and washed with water and chloroform. Recrystallization from chloroform gives 1-bromomethyl-6-phenyl-8-trifluoromethyl-4H-s-triazolo[4,3-a][1,4]benzodiazepine 5-oxide as colorless plates containing one mole of chloroform of crystallization. Melting point 185° to 210° C. (darkening).

After a similar manner to Examples 1 to 3, the following compounds are prepared from the corresponding 2-hydrazino-1,4-benzodiazepine 4-oxides:

1-Bromomethyl-8-chloro-6-(4-chlorophenyl)-4H-s-triazolo-[4,3-a][1,4]benzodiazepine 5-oxide; colorless needles (from dimethylformamide-water) melting at 264° to 269° C. (decomp.)

1-Bromomethyl-8-nitro-6-phenyl-4H-s-triazolo[4,3-a][1,4]-benzodiazepine 5-oxide; yellow prisms (from dimethylformamide-water) melting at 266° to 269° C. (decomp.)

EXAMPLE 4

To a suspension of 2.0 parts of 1-bromomethyl-8-chloro-6-phenyl-4H-s-triazolo[4,3-a][1,4]benzodiazepine 5-oxide in 20 volume parts of dimethylformamide is added 5 volume parts of 40 weight % aqueous solution of dimethylamine under stirring, and the resulting solution is stirred for 30 minutes at room temperature. After removing the solvent, the crystalline residue is recrystallized from ethyl alcohol to give 8-chloro-1-dimethylaminomethyl-6-phenyl-4H-s-triazolo[4,3-a][1,4]benzodiazepine 5-oxide as colorless prisms melting at 217° to 219° C.

After a similar manner to Example 4, the following compounds are prepared:

8-Chloro-6-(4-chlorophenyl)-1-dimethylaminomethyl-4H-s-triazolo[4,3-a][1,4]benzodiazepine 5-oxide; colorless prisms (from dimethylformamide-water) melting at 260° to 260.5° C.

1-Dimethylaminomethyl-6-phenyl-8-trifluoromethyl-4H-s-triazolo[4,3-a][1,4]benzodiazepine 5-oxide; colorless plates (from acetone-isopropyl ether) melting at 188° to 190° C.

1-Dimethylaminomethyl-8-nitro-6-phenyl-4H-s-triazolo-[4,3-a][1,4]benzodiazepine 5-oxide; yellow plates (from ethanol) melting at 228° to 230° C.

EXAMPLE 5

To a mixture of 2.85 parts of 7-chloro-2-hydrazino-5-phenyl-3H-1,4-benzodiazepine, 6.0 parts of methyl orthobromoacetate and 50 volume parts of ethyl alcohol is added dropwise 1.2 volume parts of sulfuric acid under stirring, followed by stirring for further 30 minutes at room temperature. This procedure gives 1-bromomethyl-8-chloro-6-phenyl-4H-s-triazolo[4,3-a][1,4]benzodiazepine. Then, to the reaction mixture is added 20 volume parts of 40 weight % aqueous solution of dimethylamine under ice-cooling, and the whole mixture is stirred at first for 30 minutes under ice-cooling and then for further 1 hour at room temperature. The reaction mixture is concentrated under reduced pressure, and to the residue is added water, followed by extraction with chloroform. After removing the chloroform, the resulting oily substance is treated with ethyl ether to give crystals. Recrystallization from ethyl acetate gives 8-chloro-1-dimethylaminomethyl-6-phenyl-4H-s- triazolo[4,3-a][1,4]benzodiazepine as colorless pillars melting at 168° to 169.5° C.

EXAMPLE 6

To a mixture of 2.85 parts of 7-chloro-2-hydrozino-5-phenyl-3H-1,4-benzodiazepine, 6.0 parts of methyl orthobromoacetate and 50 volume parts of ethyl alcohol is added dropwise 1.2 volume parts of sulfuric acid under stirring, followed by stirring for further 30 minutes at room temperature. This procedure gives 1-bromomethyl-8-chloro-6-phenyl-4H-s-triazolo[4,3-a][1,4]benzodiazepine. Then, to the reaction mixture is added dropwise 6 volume parts of triethylamine under stirring and ice-cooling below 10° C. and then added 5 parts of N-methylpiperazine. The whole mixture is stirred for 30 minutes under ice-cooling and further 2 hours at room temperature. The solvent is removed by distillation and to the residue is added water. Precipitated product is collected by filtration and washed with water and ethyl ether. Recrystallization from acetone gives 8-chloro-1-(4-methylpiperazino)methyl-6-phenyl-4H-s-triazolo[4,3-a][1,4]-benzodiazepine as colorless plates melting at 203° to 206° C.

After a similar manner to Example 5 or 6, the following compounds are prepared:

8-Chloro-1-methylaminomethyl-6-phenyl-4H-s-triazolo-[4,3-a][1,4]benzodiazepine; colorless prisms (from ethyl acetate) melting at 166° to 168° C.

8-Chloro-1-diethylaminomethyl-6-phenyl-4H-s-triazolo-[4,3-a][1,4]benzodiazepine; colorless prisms (from acetone-ethyl ether) melting at 130° to 132° C.

8-Chloro-1-(2-hydroxyethyl)aminomethyl-6-phenyl-4H-s-triazolo[4,3-a][1,4]benzodiazepine; colorless prisms (from acetone-benzene) melting at 162° to 164.5° C.

8-Chloro-1-[bis-(2-hydroxyethyl)]aminomethyl-6-phenyl-4H-s-triazolo[4,3-a][1,4]benzodiazepine (containing ½ mole ethyl acetate of crystallization); colorless fine needles (from ethyl acetate) melting at 84° to 87° C. (softening).

8-Chloro-1-cyclohexylaminomethyl-6-phenyl-4H-s-triazolo[4,3-a][1,4]benzodiazepine; colorless prisms (from ethyl acetate) melting at 187° to 188° C.

8-Chloro-1-morpholinomethyl-6-phenyl-4H-s-triazolo-[4,3-a][1,4-benzodiazepine; colorless prisms (from ethyl acetate) melting at 214° to 215° C.

8-Chloro-6-phenyl-1-piperidinomethyl-4H-s-triazolo-[4,3-a][1,4]benzodiazepine; colorless plates (from methanol) melting at 202° to 203° C.

8-Chloro-1-[4-(2-hydroxyethyl)piperazino]methyl-6-phenyl-4H-s-triazolo[4,3-a][1,4]benzodiazepine (hemihydrate); colorless plates (from aqueous methanol) melting at 113° to 118° C.

1-Dimethylaminomethyl-6-phenyl-4H-s-triazolo[4,3-a][1,4]-benzodiazepine; colorless prisms (from ethyl acetate) melting at 181° to 182° C.

1-Dimethylaminomethyl-8-methyl-6-phenyl-4H-s-triazolo-[4,3-a][1,4]benzodiazepine; colorless prisms (from methanol-ethyl ether) melting at 154° to 156° C.

8-Chloro-1-dimethylaminomethyl-6-(4-methoxyphenyl)-4H-s-triazolo[4,3-a][1,4]benzodiazepine; colorless prisms (from ethanol) melting at 224° to 225° C.

8-Chloro-6-(2-chlorophenyl)-1-dimethylaminomethyl-4H-s-triazolo[4,3-a][1,4]benzodiazepine; colorless plates (from ethanol) melting at 203° to 205° C.

What we claim is:

1. A compound selected from the group consisting of a compound of the formula

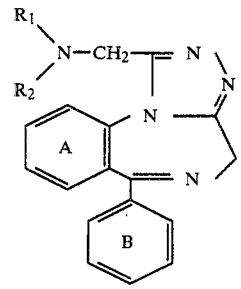

wherein $R_1$ represents hydrogen, alkyl of 1-6 carbon atoms, hydroxyalkyl of 1-6 carbon atoms, cycloalkyl of 3-6 carbon atoms or hydroxycycloalkyl of 3-6 carbon atoms, $R_2$ represents hydroxyalkyl of 1-6 carbon atoms, cycloalkyl of 3-6 carbon atoms or hydroxycycloalkyl of 3-6 carbon atoms, or $R_1$ and $R_2$, together with the adjacent nitrogen atom, form ethyleneimino, pyrrolidino, piperidino, morpholino, piperazino, N-(2-hydroxyethyl)piperazino, N-(3-hydroxypropyl)-piperazino, N-methylpiperazino or N-ethylpiperazino, the rings A and B are unsubstituted or substituted by one or more members selected from the group consisting of halogen, nitro, trifluoromethyl, alkyl of 1-3 carbon atoms and alkoxy of 1-3 carbon atoms, and the nitrogen atom at the 5-position is unsubstituted or substituted by oxygen, and a pharmaceutically acceptable salt thereof.

2. A compound as claimed in claim 1, wherein $R_1$ is hydrogen and $R_2$ is hydroxyalkyl of 1-6 carbon atoms.

3. A compound as claimed in claim 1, wherein $R_1$ and $R_2$ are each hydroxyalkyl of 1-6 carbon atoms.

4. A compound as claimed in claim 1, wherein $R_1$ and $R_2$, together with the adjacent nitrogen atom, form ethyleneimino, pyrrolidino, piperidino, morpholino, piperazino, N-(2-hydroxyethyl)piperazino, N-(3-hydroxypropyl)piperazino, N-methylpiperazino or N-ethylpiperazino.

5. A compound as claimed in claim 1, wherein the rings A and B are substituted by one or more members selected from the group consisting of halogen, nitro, trifluoromethyl, alkyl of 1-3 carbon atoms and alkoxy of 1-3 carbon atoms.

6. A compound selected from the group consisting of 8-chloro-1-(4-methylpiperazino)methyl-6-phenyl-4H-s-triazolo-[4,3-a][1,4]benzodiazepine, 8-chloro-1-(2-hydroxyethyl)aminomethyl-6-phenyl-4H-s-triazolo[4,3-a][1,4]benzodiazepine, 8-chloro-1-[bis-(2-hydroxyethyl)]aminomethyl-6-phenyl-4H-s-triazolo[4,3-a][1,4]benzodiazepine, 8-chloro-1-cyclohexylaminomethyl-6-phenyl-4H-s-triazolo[4,3-a][1,4]benzodiazepine, 8-chloro-1-morpholinomethyl-6-phenyl-4H-s-triazolo[4,3-a]-[1,4]benzodiazepine, 8-chloro-6-phenyl-1-piperidinomethyl-4H-s-triazolo[4,3-a][1,4]benzodiazepine and 8-chloro-1-[4-(2-hydroxyethyl)-piperazino]methyl-6-phenyl-4H-s-triazolo[4,3-a]-[1,4]benzodiazepine.

7. A compound selected from the group consisting of 8-chloro-1-(4-methylpiperazino)methyl-6-phenyl-4H-s- triazolo-[4,3-a][1,4]benzodiazepine, 8-chloro-1-(2-hydroxyethyl)aminomethyl-6-phenyl-4H-s-triazolo[4,3-a][1,4]benzodiazepine, 8-chloro-1-[bis-(2-hydroxyethyl)]aminomethyl-6-phenyl-4H-s-triazolo[4,3-a][1,4]benzodiazepine, 8-chloro-1-cyclohexylaminomethyl-6-phenyl-4H-s-triazolo[4,3-a][1,4]benzodiazepine, 8-chloro-1-morpholinomethyl-6-phenyl-4H-s-triazolo[4,3-a]-[1,4]benzodiazepine and 8-chloro-1-[4-(2-hydroxyethyl)piperazino]-methyl-6-phenyl-4H-s-triazolo[4,3-a][1,4]benzodiazepine.

8. A compound as claimed in claim 1, wherein the rings A and B are unsubstituted.

9. A compound as claimed in claim 1, wherein the compound is 8-chloro-1-(4-methylpiperazino)methyl-6-phenyl-4H-s-triazolo[4,3-a][1,4]benzodiazepine.

10. A compound as claimed in claim 1, wherein the compound is 8-chloro-1-(2-hydroxyethyl)aminomethyl-6-phenyl-4H-s-triazolo[4,3-a][1,4]benzodiazepine.

11. A compound as claimed in claim 1, wherein the compound is 8-chloro-1-[bis-(2-hydroxyethyl)]aminomethyl-6-phenyl-4H-s-triazolo[4,3-a][1,4]benzodiazepine.

12. A compound as claimed in claim 1, wherein the compound is 8-chloro-1-cyclohexylaminomethyl-6-phenyl-4H-s-triazolo-[4,3-a][1,4]benzodiazepine.

13. A compound as claimed in claim 1, wherein the compound is 8-chloro-1-morpholinomethyl-6-phenyl-4H-s-triazolo[4,3-a][1,4]benzodiazepine.

14. A compound as claimed in claim 1, wherein the compound is 8-chloro-6-phenyl-1-piperidinomethyl-4H-s-triazolo[4,3-a][1,4]benzodiazepine.

15. A compound as claimed in claim 1, wherein the compound is 8-chloro-1-[4-(2-hydroxyethyl)piperazino]methyl-6-phenyl-4H-s-triazolo[4,3-a][1,4]benzodiazepine.

* * * * *